(12) United States Patent
Klewinghaus (10) Patent No.: US 11,707,560 B2
(45) Date of Patent: Jul. 25, 2023

(54) BLOOD TREATMENT DEVICE FOR CARRYING OUT AN EXTRACORPOREAL BLOOD TREATMENT, BLOOD-GUIDING DEVICE, BLOOD TREATMENT SYSTEM

(71) Applicant: FRESENIUS MEDICAL CARE DEUTSCHLAND GMBH, Bad Homburg (DE)

(72) Inventor: Jurgen Klewinghaus, Oberursel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1079 days.

(21) Appl. No.: 16/468,297

(22) PCT Filed: Dec. 14, 2017

(86) PCT No.: PCT/EP2017/082783
§ 371 (c)(1),
(2) Date: Jun. 11, 2019

(87) PCT Pub. No.: WO2018/109071
PCT Pub. Date: Jun. 21, 2018

(65) Prior Publication Data
US 2020/0069859 A1 Mar. 5, 2020

(30) Foreign Application Priority Data
Dec. 15, 2016 (DE) ...................... 10 2016 014 892.6

(51) Int. Cl.
*A61M 1/34* (2006.01)
*A61M 1/26* (2006.01)
(Continued)

(52) U.S. Cl.
CPC ............ *A61M 1/3413* (2013.01); *A61M 1/16* (2013.01); *A61M 1/1698* (2013.01);
(Continued)

(58) Field of Classification Search
CPC .. A61M 1/3413; A61M 1/267; A61M 1/3434; A61M 1/3603; A61M 1/16;
(Continued)

(56) References Cited

U.S. PATENT DOCUMENTS 5,368,555 A * 11/1994 Sussman ............. A61M 1/3475
435/1.1
6,913,588 B2 * 7/2005 Weitzel ............... A61M 1/3621
604/4.01
(Continued)

FOREIGN PATENT DOCUMENTS

| CN | 103547300 A | 1/2014 |
|---|---|---|
| CN | 103857420 A | 6/2014 |

(Continued)

OTHER PUBLICATIONS

English translation of EP-2238996-A1 (Year: 2010).*
(Continued)

*Primary Examiner* — Philip R Wiest
(74) *Attorney, Agent, or Firm* — Kilyk & Bowersox, P.L.L.C.

(57) ABSTRACT

The invention relates to a blood treatment device for carrying out an extracorporeal blood treatment in which blood is guided in a blood guidance device having a main blood line and at least one secondary line, the latter being fluidically connected to the main blood line and the main blood line having a dialyzer and, downstream from the dialyzer, a blood treatment element, wherein the blood treatment device has a control device; and a pump configuration, which is equipped for generating blood flows in the main blood line and also in the at least one secondary line, wherein the control device is designed to operate the pump configuration in such a way that a first blood flow rate in the dialyzer is decoupled from a second blood flow rate in the blood treatment element. Furthermore, the invention relates to a
(Continued)

blood guidance device for cooperation with the blood treatment device as well as for a blood treatment system.

8 Claims, 6 Drawing Sheets

(51) Int. Cl.
    *A61M 1/36*     (2006.01)
    *A61M 1/16*     (2006.01)

(52) U.S. Cl.
    CPC .............. *A61M 1/267* (2014.02); *A61M 1/34* (2013.01); *A61M 1/342* (2013.01); *A61M 1/3434* (2014.02); *A61M 1/3441* (2013.01); *A61M 1/3496* (2013.01); *A61M 1/3603* (2014.02); *A61M 1/3621* (2013.01); *A61M 1/3626* (2013.01); *A61M 1/3639* (2013.01); *A61M 1/3653* (2013.01); *A61M 1/3666* (2013.01); *A61M 1/3679* (2013.01); *A61M 2202/203* (2013.01); *A61M 2202/206* (2013.01); *A61M 2205/0238* (2013.01); *A61M 2205/12* (2013.01); *A61M 2205/3334* (2013.01); *A61M 2205/3337* (2013.01); *A61M 2205/7509* (2013.01); *A61M 2205/7518* (2013.01); *A61M 2250/00* (2013.01)

(58) Field of Classification Search
    CPC ...... A61M 1/1698; A61M 1/34; A61M 1/342; A61M 1/3441; A61M 1/3496; A61M 1/3621; A61M 1/3626; A61M 1/3639; A61M 1/3653; A61M 1/3666; A61M 1/3679; A61M 2202/203; A61M 2202/206; A61M 2205/0238; A61M 2205/12; A61M 2202/3334; A61M 2205/3337; A61M 2205/7509; A61M 2205/7518
See application file for complete search history.

(56) References Cited

U.S. PATENT DOCUMENTS

| | | | |
|---|---|---|---|
| 2005/0182349 A1* | 8/2005 | Linde | A61M 1/3489 604/4.01 |
| 2005/0236329 A1* | 10/2005 | Brotherton | A61M 1/3489 210/651 |
| 2009/0099498 A1 | 4/2009 | Demers et al. | |
| 2010/0288703 A1 | 11/2010 | Fortenberry | |
| 2012/0330214 A1 | 12/2012 | Peters et al. | |
| 2014/0083943 A1 | 3/2014 | Nuernberger | |
| 2014/0088483 A1 | 3/2014 | Fontanazzi et al. | |
| 2014/0238912 A1 | 8/2014 | Vincent | |

FOREIGN PATENT DOCUMENTS

| | | | | |
|---|---|---|---|---|
| CN | 104755114 A | 7/2015 | | |
| EP | 2238996 A1 * | 10/2010 | ......... | A61B 5/02141 |
| WO | 2016103290 A1 | 6/2016 | | |

OTHER PUBLICATIONS

International Preliminary Report on Patentability issued in corresponding International Patent Application No. PCT/EP2017/082783 dated Jun. 18, 2019 (8 pages).

Office Action issued in corresponding Chinese Patent Application No. 201780077600.X dated Jun. 17, 2021 (English translation only) (7 pages).

International Search Report and Written Opinion issued in corresponding International Patent Application No. PCT/EP2017/082783 (with English translation of International Search Report) dated Mar. 23, 2018 (11 pages).

Office Action issued in corresponding European Patent Application No. 17828684.5 dated Jul. 27, 2022 (8 pages).

* cited by examiner

BLOOD TREATMENT DEVICE FOR CARRYING OUT AN EXTRACORPOREAL BLOOD TREATMENT, BLOOD-GUIDING DEVICE, BLOOD TREATMENT SYSTEM

This application is a National Stage Application of PCT/EP2017/082783, filed Dec. 14, 2017, which claims priority to German Patent Application No. 10 2016 014 892.6, filed Dec. 15, 2016.

The present invention relates to a device for carrying out an extracorporeal blood treatment, a blood guidance device for cooperating with a blood treatment device as well as a blood treatment system.

It is known in the field of extracorporeal blood treatment that various therapies can be combined in a single therapy, which can be carried out by means of a single medical treatment device and/or a single medical treatment system, for example. In other words, the blood withdrawn is treated, preferably in various ways, by using at least two separate blood treatment elements in a joint extracorporeal blood circulation. Such a therapy is known as a combination therapy. Therapies having medical indications that are causally related and therefore often occur jointly are usually combined. In addition, a combination of therapies is also recommended for various indications when the treatment technique justifies combining them in this way due to advantageous synergies.

Thus, for example, the combination of renal substitute therapies with other extracorporeal blood therapies is used in the field of extracorporeal blood treatments. For example, treatment of acute dialysis (CRRT) such as hemodialysis (HD), hemodiafiltration (HDF), hemofiltration (HF), hemoperfusion (HP) or ISO-UF are used in a joint extracorporeal blood circulation in combination with treatments of the extracorporeal membrane oxygenation and/or removal of $CO_2$. In most cases, a dialyzer and a blood treatment element for another extracorporeal blood therapy, such as a gas exchanger, are therefore disposed in series in a joint extracorporeal blood circulation.

Furthermore, it is known that the efficacy of the gas exchange, in particular for the removal of $CO_2$ from the blood or for the enrichment of $O_2$ in the blood increases with an increase in the flow rate.

The inventor has recognized that the necessary coupling of flow rates in the dialyzer and in the gas exchanger is problematical due to the serial arrangement of the two components independently of their order is problematical for the operation of the treatment device with an effective gas exchange. For example, the flow rates used in the continuous treatment methods of acute dialysis (CRRT) do not usually exceed 200-300 mL/min. However, the efficiency of the aforementioned pulmonary support therapies depends greatly on the blood flow rate. In the case of extracorporeal membrane oxygenation (ECMO), the oxygenation rate can be kept close to zero at a blood flow rate of less than 500 mL/min. The blood flow rates that are used with pure ECMO methods are therefore usually substantially greater than 1 L/min. Removal of $CO_2$ is possible at even lower blood flow rates but, here again, the range generally used is only above approximately 500 mL/min. A combination of these renal substitute therapies and pulmonary support therapies in the prior art is thus always associated with the fact that one of the basic indications is being treated with a reduced efficiency.

However, the aforementioned problem is not limited to a combination of renal substitute and pulmonary support therapies but instead is always encountered whenever a dialyzer is operated in combination with a blood treatment element for an extracorporeal blood therapy in an extracorporeal blood circulation, wherein the dialyzer and the blood treatment element each have different requirements regarding the blood flow for an optimum treatment efficiency.

The object of the present invention is to overcome the aforementioned disadvantages and to permit an extracorporeal blood treatment using a combination of a dialyzer and another blood treatment element (combination therapy) in the optimum efficiency range for each partial therapy.

According to the invention the object is achieved by the devices according to the independent claims. The dependent claims each additionally contain advantageous embodiments of the invention.

The blood treatment device according to the invention for carrying out an extracorporeal blood treatment in which blood is passed through a blood guidance device having a main blood line and at least one secondary line which is fluidically connected to the main blood line and wherein the main blood line has a dialyzer and downstream from the dialyzer a blood treatment element, also having a control device and a pump configuration which is equipped for generating blood flows in the main blood line and in the at least one secondary line wherein the control device is configured to operate the pump configuration in such a way that a first blood flow rate in the dialyzer (dialyzer flow rate) is uncoupled from a second blood flow rate in the blood treatment element.

The blood guidance device according to the invention for cooperating with a blood treatment device according to the invention has a main blood line for fluidic connection to a dialyzer and for fluidic connection to a blood treatment element downstream from the dialyzer, wherein the main blood line has a blood sampling port for connection to a blood withdrawal access of a patient at one end, and at the other end it has a blood return port for connection to a blood return access of the patient, at least one secondary line, which leads away from the main blood line at a first branch and combines with the main blood line again at a second branch and one or more pump configuration segments formed for action of the pump configuration of the blood treatment device.

The blood treatment system according to the invention has a blood treatment device according to the invention and a blood guidance device according to the invention.

In other words, the blood treatment device according to the invention as well as the blood guidance device and the blood treatment system according to the invention make it possible to improve the operation of an extracorporeal blood treatment with regard to the efficiency of the treatment, utilizing a common extracorporeal blood circulation in a series connection of a dialyzer to a blood treatment element disposed downstream from the dialyzer for another extracorporeal blood treatment. For the additional extracorporeal blood therapy, a higher blood flow than that used for therapy in the dialyzer is appropriate.

The blood treatment element for the additional extracorporeal therapy may be a gas exchange unit for enrichment of $O_2$ and/or removal of $CO_2$. The blood treatment element may also be an adsorber cartridge for therapeutic apheresis. The blood treatment element may also be a diagnostic element which can determine parameters of the blood for detecting the existence of pathological changes in the blood. All treatment elements acting on the blood can represent the blood treatment element in the sense of this specification. The effect may be a mechanical, chemical, physical or other effect.

In the sense of this specification, "therapy" may include not only a cure but also at least relief, symptomatic therapy, postponement, drug withdrawal and diagnosis. In particular, a blood therapy may be understood to include any effect on blood or change in blood, such as adding substances to blood or removing substances from blood that can cause one of the aforementioned effects or a corresponding effect.

Use of a joint extracorporeal blood circulation for both treatments in the sense of a combination theory is desirable because with this the invasive steps of withdrawal of blood and the return of the blood for both therapies must be performed only once and therefore the patient is also exposed to the associated treatment risks only once.

With the arrangement of the dialyzer and the blood treatment element in series in an extracorporeal blood circulation, basically two sequences are possible. However, if the blood flows first through the gas exchanger and then the dialyzer, for example, in the case of removal of $CO_2$ as the additional extracorporeal blood treatment, then after passing through the gas exchanger, the blood which already has a low $CO_2$ content after passing through the gas exchanger may undergo a re-enrichment with $CO_2$. This is achieved due to the concentration gradient across the dialyzer membrane because dialysis solutions usually contain bicarbonate in which $CO_2$ is present in a buffered form. If the blood passes through the gas exchanger downstream from the dialyzer, then this re-enrichment does not occur.

The blood treatment device may represent the reusable machine side of the blood treatment system. The blood guidance device may constitute a blood tubing set or a cassette with blood lines or a combination of blood tubings and at least one cassette with blood lines for furnishing equipment on the blood treatment device. The blood guidance device here may be designed as a disposable medical article that is discarded after each treatment for hygienic reasons. In particular, the blood guidance device may also have one or more additional fluid guides in addition to the blood guide, such as a dialyzer circulation or lines for guiding a sweep gas during operation of a gas exchanger.

The main blood line of the blood guide device may have suitable connectors or connections for connecting to the dialyzer and/or for connecting to the blood treatment element. The design of these connectors, in particular for connection to the dialyzer, may comprise, for example, a cylindrical shape with an outside diameter in the range of 10.5-12.8 mm as well as a conical fluid channel with an inside diameter of 6.33 mm at the distal end of the connector. According to the invention, however, other embodiments are also conceivable, which fulfill the requirements of the intended flow rates according to the knowledge of those skilled in the art. In addition, the blood guidance device may also comprise the dialyzer and/or the blood treatment element when they are connected to the main blood line, for example, by adhesive bonding or welding.

The devices for blood treatment according to the invention and for blood guidance according to the invention may be provided to work together and they may jointly form a system for treatment of blood according to the invention. The blood treatment system may also comprise other components in addition to the blood treatment device and the blood guidance device.

The devices for blood treatment and for blood guidance may each have certain complementary components for cooperation. Thus, for example, the blood treatment device has a pump configuration while the blood guidance device has one or more pump configuration sections designed for acting on the pump configuration of the blood treatment device.

Optionally the blood treatment device in some embodiments may have one or more pressure sensors or a blood guidance device may optionally have one or more pressure measurement sections in some embodiments, which may be designed for determining the pressure by means of the aforementioned pressure sensors of the blood treatment device for measurement of the pressure. The pressure measurement section may be a flexible membrane or a branch line, which can transfer the pressure in the blood guidance device to the pressure sensor through a compressible gas column.

Furthermore, in some embodiments, the blood treatment device may optionally have an infusion pump for supplying a medical fluid or two infusion pumps for supplying medical fluid or three infusion pumps for supplying medical fluid or four or more infusion pumps for supplying medical fluid, while the main blood line of the blood guidance device in some embodiments may optionally have one or more injection ports for medical fluid for anticoagulation as well as optionally one or more injection ports for dilution fluid.

An injection port here may be understood to be a simple connector to the main blood line of the blood guidance device, for example, designed as a Luer lock but also a releasably or fixedly connected access line to the main blood line. The infusion pumps of the blood treatment device mentioned above may be provided for having a pump action on the access lines connected to the injection ports. The access lines may each be connected to fluid reservoirs with the added fluid for delivery of said fluid in the main blood line by means of the infusion pumps.

In one embodiment, the inventor proposes that the main blood line of the joint extracorporeal blood circulation should branch at a first branch upstream from the dialyzer, a second line should lead around the dialyzer and should combine with the main blood line again at a second branch downstream from the dialyzer and upstream from the gas exchanger. In this way, the inventor has placed the dialyzer upstream from the gas exchanger in the main blood line. The result of this may be that the re-enrichment with $CO_2$ described above can be prevented.

In addition, a pump system may be disposed on the extracorporeal blood circulation, said pump system being equipped to generate blood flows in the main blood line and in the secondary line. To do so, the pump system may be connected to a control device. The control device is configured to control the operation of the pump system through corresponding signals. In the sense of the description as a whole, the term "control" also refers to the possibility of regulation as an alternative.

The control device is configured to operate the pump system in such a way that a first blood flow rate in the dialyzer is decoupled from a second blood flow rate in the blood treatment element. The term "decoupled" here is understood to mean that any desired flow rates can be created in the dialyzer and in the blood treatment element by means of this control without limiting the choice of the other flow rate.

In other embodiments, the pump system may be designed to generate blood flow rates that are independent of one another in the main blood line and in the secondary line. The term "independent" here is understood to mean that selection of one of the two flow rates has no effect on the setting of the pump system for the choice of the other flow rate.

Those skilled in the art will recognize that the pump system may be designed in a variety of ways to act in the aforementioned manner.

In general, the pump system has at least two elements, which act on the flow in the two line segments. At least one of these elements is usually an active element through which the flow can be induced in a line element, for example, a pump. The second one of the at least two elements may also be an active element for generating a flow or a passive element, whose effect may consist of the fact that the flow is defined or can be adjusted by the element. This second element may be, for example, a throttle or a valve.

For example, the pump system may consist of an occlusive blood pump in the main blood line upstream from the first branch and an additional occlusive blood pump downstream from the first branch and upstream from the dialyzer. Additional exemplary embodiments of the pump system are included in the figures and in the description of the figures. However, in addition to the embodiments described as examples here, the invention also includes all other pump systems capable of carrying blood through the main blood line and/or the at least one secondary line.

In additional embodiments of the invention, the pump system may also be equipped to generate a blood flow in a second secondary line. The control device in this case may be configured to operate the pump system in such a way that the blood flow rate in at least one segment of the main blood line is independent of at least one of the blood flow rates in the secondary lines.

In another embodiment, the main blood line of the joint extracorporeal blood circulation branches at a first branch downstream from the blood treatment element for the additional extracorporeal blood treatment, a secondary line leads around the blood treatment element and is combined with the main blood line again upstream from the blood treatment element and downstream from the dialyzer. In this case the pump system with the blood flow in the secondary line creates a recirculation of the blood flow through the blood treatment element. The blood flow rate in the blood treatment element is increased in comparison with the blood flow rate in the dialyzer by the amount of the blood flow in the secondary line, which leads to the decoupling of the two flow rates according to the invention and therefore to a solution to the problem.

In the case of removing $CO_2$, the extracorporeal blood, in its passage through the gas exchanger, is first reduced mainly by the $CO_2$ freely available in the plasma. Next, free $CO_2$ is again discharged from the natural $CO_2$ buffer system of the blood into the plasma. The additional reduction in the partial pressure of the free $CO_2$ is thus compensated after a while. The inventor has recognized that the blood already treated in the gas exchanger is thus accessible for renewed treatment after a short period of time, and for this reason, it may be worthwhile to recirculate the blood through the gas exchanger as described above.

In additional embodiments of the invention, the blood may also be passed through two secondary lines, wherein the first secondary line is separated from the main line at a first branch upstream from the dialyzer and combines again with the main blood line at a second branch downstream from the dialyzer and upstream from the treatment element. The second secondary line may branch off from the main blood line at a recirculation branch at a recirculation branch downstream from the blood treatment element and open into a recirculation return port. The recirculation return port may be disposed here in the main blood line upstream from the connection point for the blood treatment element and downstream from the connection point for the dialyzer. Furthermore, the circulation return port may also be disposed in the first secondary line upstream from the second branch. In these embodiments, the second secondary line can recirculate the blood through the blood treatment element for the additional blood treatment therapy and may thus contribute toward an increase in the efficiency of this partial therapy. In these embodiments, the pump configuration may also be equipped to generate a blood flow in the second secondary line. Furthermore, the control device may be configured to operate the pump configuration in such a way that the blood flow rate in at least one section of the main blood line is independent of at least one of the blood flow rates in the secondary lines.

In extracorporeal blood therapies, measures may be taken to counteract coagulation of the blood. To do so, the patient is usually treated systemically with an anticoagulant substance such as heparin, or local anticoagulation may be administered in the extracorporeal blood circulation, for example, by means of heparin or by addition of citrate and calcium (Ci-Ca anticoagulation). Anticoagulant coatings on the blood-carrying components of the extracorporeal blood circulation are also widely used. The method using Ci-Ca anticoagulation has also been established for many years in the field of acute dialysis, where dosing has been optimized and reviewed extensively in long-term studies. The coagulant effect on blood is usually reduced by binding calcium ions in so-called citrate calcium chelates by addition of citrate in the extracorporeal blood circulation upstream from the dialyzer. In some cases, these citrate calcium chelates are infused into the patient again together with the return of the blood, where the citrate components are metabolized in the liver and the calcium is released again. Another fraction of the chelates is removed from the extracorporeal blood circulation by the dialyzer membrane and discarded.

Since the patient loses a significant amount of calcium in this process, calcium may be added artificially prior to the reinfusion of blood. The rate of citrate addition is usually linked to the blood flow rate in order to provide an adequate anticoagulant effect for the corresponding amount of blood coming in contact with the components of the extracorporeal blood circulation. The rate of addition of calcium may be selected so that the calcium losses via the dialyzer membrane are compensated. It thus depends on the blood flow through the dialyzer, but also depends on multiple other parameters, such as the rate of addition of citrate and the individual properties of the treatment, such as the choice of the dialyzer membrane, the prevailing transmembrane pressure, etc.

Therefore, the concentration of calcium ions can be monitored regularly by taking samples during the Ci-Ca CRRT, and the rate of addition can be corrected accordingly. Furthermore, however, the experience from the studies referenced above can be utilized; these studies were carried out using standard protocols for Ci-Ca dosing, which are available to the users. To do so, a control device may be provided to control the corresponding addition of the anticoagulant substance. This control may be achieved, for example, on the basis of at least one or more of the following variables, which are described above: calcium ion concentration, blood flow rate, dialyzer membrane, transmembrane pressure and/or standard protocols saved in the device.

If another extracorporeal blood treatment is added in a joint extracorporeal blood circulation for acute dialysis, then the result may be some entirely new boundary conditions may with regard to the dosing of citrate and calcium in Ci-Ca anticoagulation. In particular, the dosing protocols established from long-term study results in a series connection of the dialyzer and the blood treatment element need not necessarily be accepted for further extracorporeal treatment because neither the influence of the blood treatment element on stimuli for coagulation nor any calcium losses beyond those known in the dialyzer are taken into account therein.

The line guidance according to the invention optionally provides the arrangement of an injection port for delivering a first medical fluid for anticoagulation, for example, citrate in a segment of the main bloodline upstream from the dialyzer, whose total blood flow will then also pass through the dialyzer. Thus, one may continue to use the known dosing protocols for Ci-Ca anticoagulation, despite the combination therapy, because at first only coagulation by the dialyzer need be taken into account. The components of the blood treatment element can be treated with an anticoagulant by coating.

Furthermore, the line guidance optionally provides the arrangement of an injection port for adding a second medical fluid for anticoagulation, for example, calcium, to the main blood line downstream from the blood treatment element.

In additional embodiments of the invention, in which the first branch is disposed upstream from the dialyzer and thus the first injection port for the first medical fluid is situated downstream from the first branch, an additional injection port for a third medical fluid for anticoagulation, for example, citrate, may be disposed upstream from the first branch. An increased anticoagulant effect in the entire extracorporeal blood circulation can be created briefly in case of need by further addition of citrate, preferably small amounts of citrate, through this line. For small amounts of citrate, the further addition of citrate through the injection port upstream from the first branch preferably takes place because the maximum amount of citrate tolerated is limited metabolically, and the greater effect is needed on the dialyzer, which does not usually have an anticoagulant coating. Therefore, in dosing calcium, it is not necessary to deviate from the known algorithm in this case, even if there is further addition of small amounts of citrate through this line.

The first and/or second and/or third medical fluid for anticoagulation may also be heparin or some other medical fluid having an anticoagulant effect.

Pump sections for infusion pumps, with which the respective fluid to be added may be delivered from a reservoir through the feed line to the main blood line, are disposed in some or all of the aforementioned injection ports for calcium or citrate, for example. In the embodiments in which the same medical fluid is delivered through multiple feed lines, in particular in the case of citrate, it is also possible to deliver the fluid with a joint pump and/or from a joint reservoir.

To determine the transmembrane pressure, the blood treatment device may have a pressure sensor as described above, in particular for measuring the pressure in the main blood line between the dialyzer and the blood treatment element, where a corresponding pressure measurement section for determining the pressure by means of the pressure sensor may be disposed in some embodiments of the blood guidance device.

The blood treatment device may have an additional pressure sensor for determining the transmembrane pressure, in particular for measuring the pressure in the main blood line between the first branch and the dialyzer. A corresponding pressure measurement section for determining the pressure by means of the pressure sensor may be disposed at the aforementioned location.

To determine the transmembrane pressure, the blood treatment device may have a pressure sensor as described previously, in particular for measuring the pressure in the main blood line between the dialyzer and the blood treatment element, where a corresponding pressure measurement section for determining the pressure by means of the pressure sensor may be disposed in some embodiments of the blood guidance device.

As described previously, the blood treatment device may have an additional pressure sensor for determining the transmembrane pressure, in particular for measuring the pressure in the main blood line between the first branch and the dialyzer. A corresponding pressure measurement section for determining the pressure by means of the pressure sensor may be disposed at the aforementioned site.

Two or more pressure sensors may also be provided at other locations for measuring the pressure at both of the aforementioned sites or also at other sites. This permits an especially accurate determination of the transmembrane pressure as well as better monitoring of the treatment process by means of limit value windows of the respective pressure values.

One or more pressure sensors may be disposed on the dialysate side for measurement of the transmembrane pressure. The pressure can thus be measured upstream and/or downstream from the dialyzer on the dialysate side.

To also allow combination therapy on the renal replacement therapy side as well as with the methods of hemofiltration or hemodiafiltration, the blood guidance device may also optionally comprise one or more injection ports for a dilution fluid on the main blood line. Through these injection ports, a dilution fluid, for example, a substitute solution or a dialysis solution may be delivered into the main blood line through these injection ports by means of corresponding infusion pumps on the side of the blood treatment device. The invention may optionally also comprise one or more reservoirs, for example, disposable bags for storage of the dilution fluid. Alternatively, the blood treatment device may also be equipped to prepare the substitute solution and/or the dialysis solution. To do so, the blood treatment device may have a water processing device with a degassing device, for example, and concentrate ports for connecting concentrate sources. An injection port for a dilution fluid may be disposed on the main blood line upstream from the dialyzer for predilution. For post-dilution, an injection port for a dilution fluid may be disposed downstream from the dialyzer and upstream from the blood treatment element. In the case of the invention combination therapy with a dialyzer and a blood treatment element, there is also another possibility for post-dilution. An injection port for a dilution fluid for post-dilution may also be disposed in the main blood line downstream from the blood treatment element. The introduction of the substitute, which usually contains calcium downstream from the blood treatment element, has the advantage that the anticoagulant effect of the citrate occurs in the widest possible parts of the extracorporeal blood circulation.

Substituate lines may also be connected by the user optionally to one or more of the aforementioned injection ports for the dilution fluid. The dilution fluid may also be delivered from a joint reservoir and/or by means of a joint infusion pump.

The present invention will now be described in greater detail below on the basis of exemplary embodiments and drawings.

Figure 1:
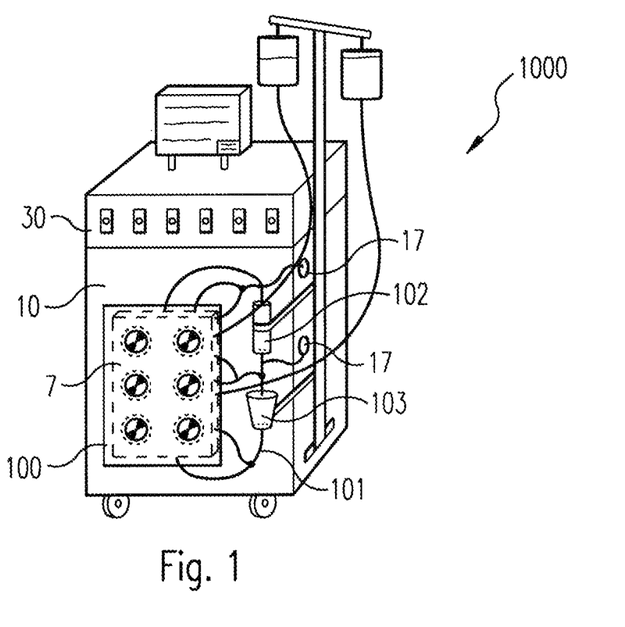
FIG. 1: shows a schematic diagram of one embodiment of a blood treatment system according to the invention.

As shown in FIG. 1, the blood treatment system 1000 has a blood treatment device 10 and a blood guidance device 100. FIG. 1 shows the blood treatment device 10 in the form of a dialysis machine for acute dialysis, equipped with a blood guidance device 100 designed as a cassette. The blood treatment device has a control device 30 and a pump configuration 7. In addition, FIG. 1 shows the main blood line 101 of the blood guidance device 100, to which a dialyzer 102 and a blood treatment element 103 in the form of a gas exchanger are connected. The main blood line 101 may also have one or more pressure measurement segments at which the pressure can be determined by means of the pressure sensors 17 that are optionally present in the blood treatment device 10.

Figure 2:
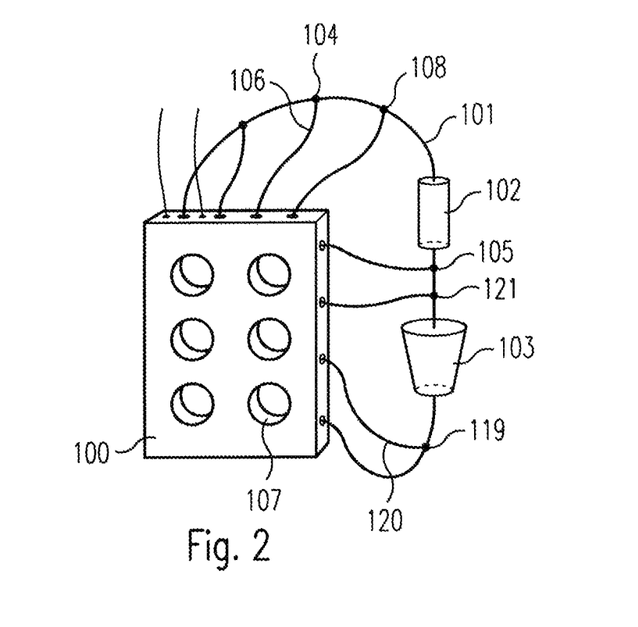
FIG. 2: shows a schematic diagram of one embodiment of a blood guidance device according to the invention, comprising a connected dialyzer and a connected blood treatment element.

According to the invention, the blood guidance device 100 may be designed as a medical disposable item in the form of a blood cassette (FIG. 2). The blood guidance device 100 may have one or more pump configuration segments 107 on which the pump configuration 7 of the blood treatment device 10 can act to deliver the fluid in the corresponding line segment of the blood treatment device 100. FIG. 2 shows the main blood line 101, which branches off from the cassette body of the blood guidance device 100, comprising the dialyzer 102 and the blood treatment element 103, namely here in the form of a gas exchanger, in series and then recycling it back to the cassette body, where the pump configuration segments 107 may be disposed. The first branch 104 from which the first secondary line 106 branches off may be disposed upstream from the dialyzer 102. The second branch 105, where the first secondary line 106 again combines with the main blood line 101 may be disposed downstream from the dialyzer 102 and upstream from the blood treatment element 103. Furthermore, an injection port 108 for a first medical fluid for anticoagulation such as citrate may be disposed upstream from the dialyzer 102. Downstream from the blood treatment element 103 a recirculation branch 119 may be disposed, from which the second secondary line 120 branches off. The second secondary line 120 opens into a recirculation return port 121 which may be disposed in the main blood line 101 upstream from the blood treatment element 103 and downstream from the dialyzer 102.

The blood guidance device 100 has a main blood line 101, wherein the main blood line 101 has a blood withdrawal port 127 at one end for connection to a blood withdrawal access of a patient and at the other end a blood return port 128 for connection to a blood return access of the patient. In the main blood line 101, the blood withdrawn from the patient can be sent in the extracorporeal circulation to the dialyzer 102 and to the blood treatment element 103 for further extracorporeal blood treatment therapy as well as being infused back into the patient, as indicated schematically by the flow plan in FIG. 3a.

Figure 3A:
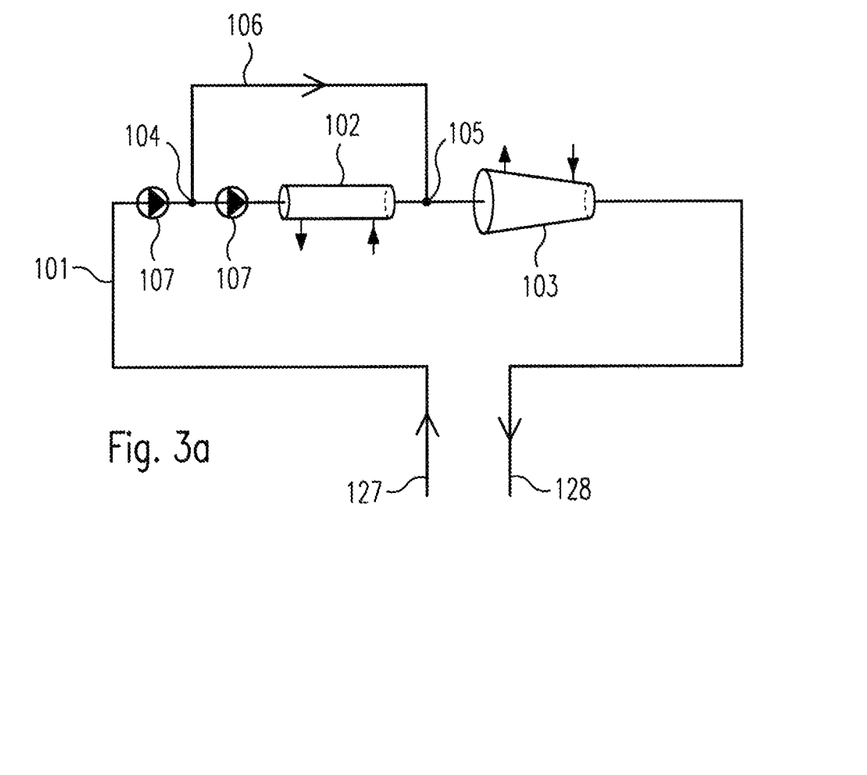
FIG. 3a: shows in a schematic diagram the flow plan of a blood guidance device according to the invention.

A dialyzer 102 is disposed in the main blood line. It usually has a blood chamber and a dialysate chamber (not shown here), wherein the two chambers are separated by a semipermeable membrane through which the blood can interact osmotically with the dialysis solution flowing in the dialysate circulation. According to the invention, the dialyzer may also be used for other renal support and/or renal replacement therapies that are customary in dialysis, such as, for example, hemodiafiltration, hemodialysis, hemoperfusion, hemofiltration, ISO-UF, etc., in particular also for therapy methods in which no dialysis solution is delivered on the dialysate side.

Downstream from the dialyzer 102, the main blood line 101 carries blood through a blood treatment element 103, designed here as a gas exchanger. The latter has a blood chamber and a gas chamber (not shown here), wherein the two chambers are separated by a semipermeable membrane through which the blood can interact osmotically with the gas flowing in the gas line.

Dialyzer 102 as well as gas exchanger 103 may have a plurality of individual membranes in the form of hollow fibers. Individual chambers for blood, dialysate or gas in the sense of the present invention may also consist of a plurality of individual volumes, which are situated inside the hollow fibers and are connected fluidically to one another at the ends of the fibers.

Upstream from the dialyzer 102, the main blood line 101 has a first branch 104. A first secondary line 106 leads from this first branch 104 to a second branch 105 of the main blood line 101.

Furthermore, the blood guidance device has pump configuration sections 107, to which the blood can be delivered by means of the pump configuration 7 of the blood treatment device 10 through the main blood line 101 and also through the first secondary line 106. In the exemplary embodiment shown in FIG. 3a, the first pump configuration 7 is shown in the form of two occlusive blood pumps, one blood pump being situated upstream from the first branch 104 in the main blood line 101 and the second blood pump being situated in the main blood line 101 downstream from the first branch 104 and upstream from the dialyzer 102. In this exemplary embodiment, the first pump delivers the fluid at the rate of 500 mL/min, for example, while the second pump delivers the fluid at only 200 mL/min. Thus, a flow rate of 300 mL/min is established in the secondary line 106. A blood flow rate of 200 mL/min is established on the dialyzer 102, and the gas exchanger 103 has 500 mL/min flowing through it because the two partial flows of 200 mL/min and 300 mL/min are combined at the second branch 105.

Figure 3B:
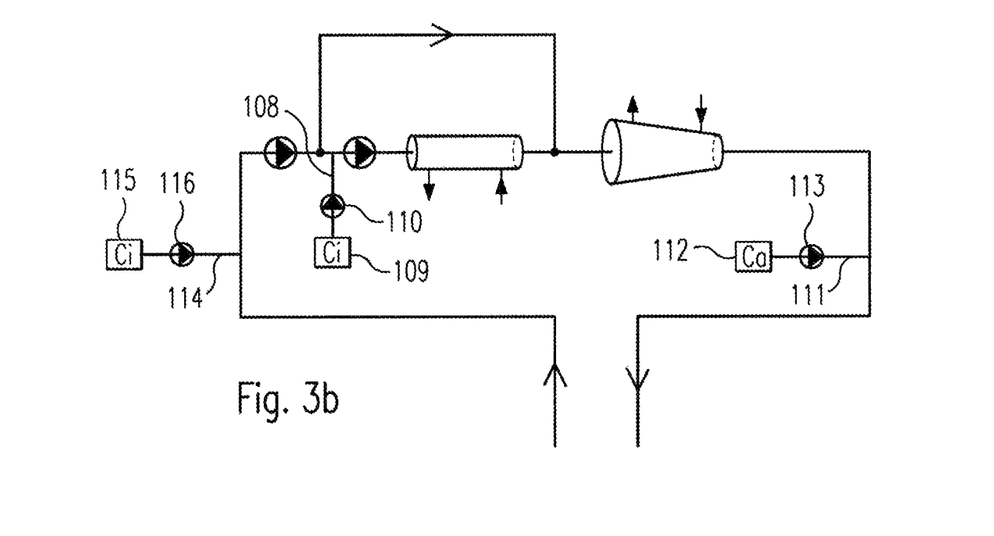
FIG. 3b: shows in a schematic diagram the flow plan of the blood guidance device illustrated in FIG. 3a with additional optional components.

As shown schematically in FIG. 3*b*, the blood guidance device may optionally have injection ports for medical fluid for anticoagulation. Thus, an injection port 108 for citrate solution may be disposed downstream from the first branch 104 and upstream from the dialyzer 102. The injection port may also be designed as a citrate line 108, which is connected to a citrate reservoir 109. Furthermore, the blood treatment device 10 may have an infusion pump 110, which is designed to deliver citrate out of the reservoir 112 and through the injection port 108 into the main blood line 101. An injection port 111 for calcium solution may also be provided downstream from the blood treatment element 103. The injection port may also be designed as a calcium line 111, which is connected to a calcium reservoir 112. Furthermore, the blood treatment device 10 may have another infusion pump 113 which is designed to deliver calcium out of the reservoir 112 via the access port 111 and into the main blood line 101.

FIG. 3*b* also shows another optional citrate addition possibility. Therefore, a third injection port 114 for the medical fluid for anticoagulation is disposed upstream from the first branch 104 in the main blood line. The injection port 114 may also be designed as a delivery line, which may be connected to a citrate reservoir 115. Furthermore, the blood treatment device 10 may have another infusion pump 116, which is designed to deliver citrate out of the reservoir 115 and into the main blood line 101 by way of the injection port 114. Alternatively, the third feed line 114 can also be supplied from the first reservoir 109 (not shown here). In addition, also as an alternative, the third infusion pump 116 may be omitted if the pressure created by the first infusion pump 110 is used in a third feed line branching off from that downstream. To do so, the third delivery line may have a valve or a throttle, which adjusts the pressure accordingly.

FIGS. 4*a* to 4*d* each show schematically a detail of the main blood line 101 of the blood guidance device 100 in the region around the first branch 104 and the second branch 105, which in this embodiment contains the two flow paths through the secondary line 106 and through the section of the main blood line 101 through the dialyzer 102. FIGS. 4*a* to 4*d* show examples of various possible embodiments of the pump configuration, represented by the pump configuration sections 207, 307, 407, 507 for the action of the pump configuration 7 of the blood treatment device 10.

Figure 4A:
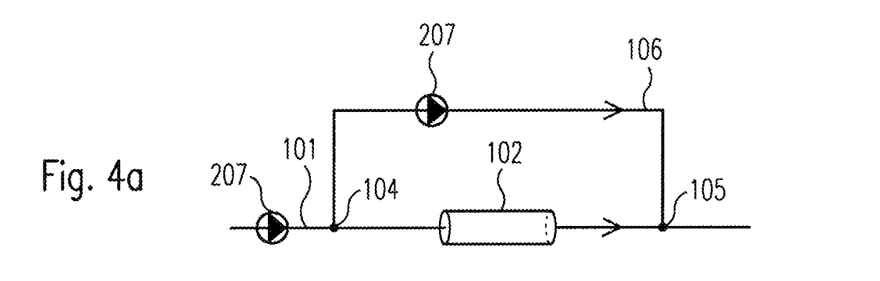
FIG. 4a: shows in a schematic diagram of the flow plan an alternative embodiment variant of the pump configuration as an example, represented by the pump configuration segments.

Whereas the pump configuration of the embodiment illustrated in FIG. 3*a*, represented by the pump configuration sections 107, has an occlusive blood pump in the main blood line 101 upstream from the first branch 104 and another occlusive blood pump in the main blood line 101 between the dialyzer 102 and the first branch 104, FIG. 4*a* shows a variant of the pump configuration represented by the pump configuration sections 207, which also has a first blood pump in the main blood line 101 upstream from the first branch 104 but with an alternative arrangement of the additional occlusive blood pump in the secondary line 106.

Figure 4B:
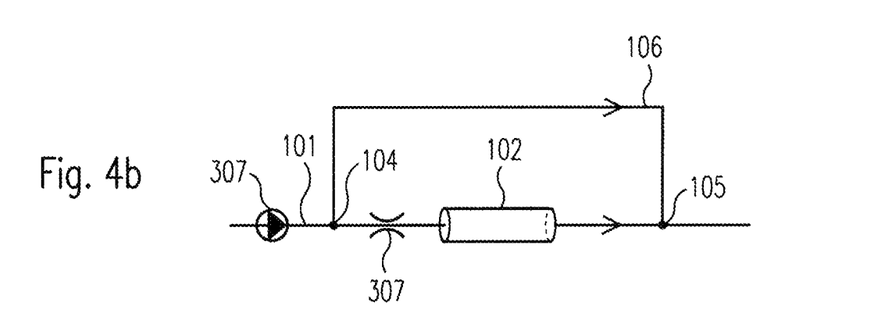
FIG. 4b: shows in a schematic diagram of the flow plan another alternative embodiment variant of the pump configuration as an example, represented by the pump configuration sections.
Figure 4C:
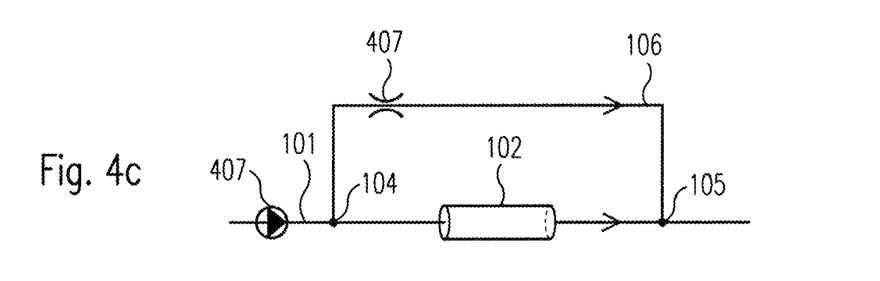
FIG. 4c: shows in a schematic diagram of the flow plan another alternative embodiment variant of the pump configuration as an example, represented by the pump configuration sections.

In the examples of pump configurations shown in FIGS. 4*b* and 4*c*, represented by the pump configuration sections 307, 407, the additional blood pumps in the secondary line 106 and/or in the main blood line 101 between the dialyzer 102 and the first branch 104 have each been replaced by throttle elements.

Figure 4D:
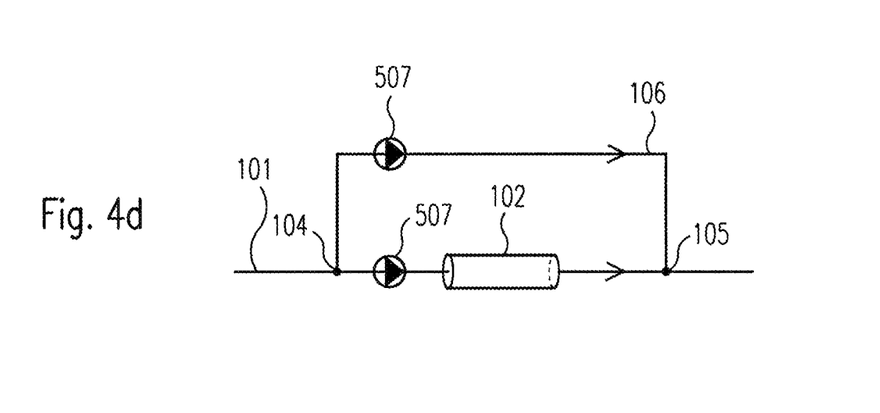
FIG. 4d: shows in the schematic diagram of the flow plan an additional alternative embodiment variant of the pump configuration represented by the pump configuration sections.

FIG. 4*d* shows another exemplary embodiment of a first pump configuration, represented by the pump configuration sections 507, comprising two occlusive blood pumps, one of which is disposed in the secondary line 106 and the other of which is situated between the dialyzer 102 and the first branch 104 in the main blood line 101.

All the pump configurations according to the invention can both generate a blood flow in the main blood line 101 and also carry a partial flow at a defined flow rate through the secondary line 106, so that the ratio between the total flow in the main blood line 101 upstream from the first branch 104 and/or downstream from the second branch 105 and in the area of the dialyzer 102 is adjustable. The invention is not limited to the embodiments of the pump configuration 7 shown in FIGS. 4*a* to 4*d*. As those skilled in the art will recognize, there are numerous other possibilities in the prior art for controlling the ratio of the flow rates in the two line sections. In many embodiments, the pump configuration 7 can control the flow rates of the two line sections independently of one another. The pump configuration 7 may have various fluidic components including occlusive pumps, non-occlusive pumps, clamps, valves, throttles, etc. The components of the pump configuration 7 may also be disposed at other locations in the extracorporeal blood circulation or may act at those locations.

Figure 5A:
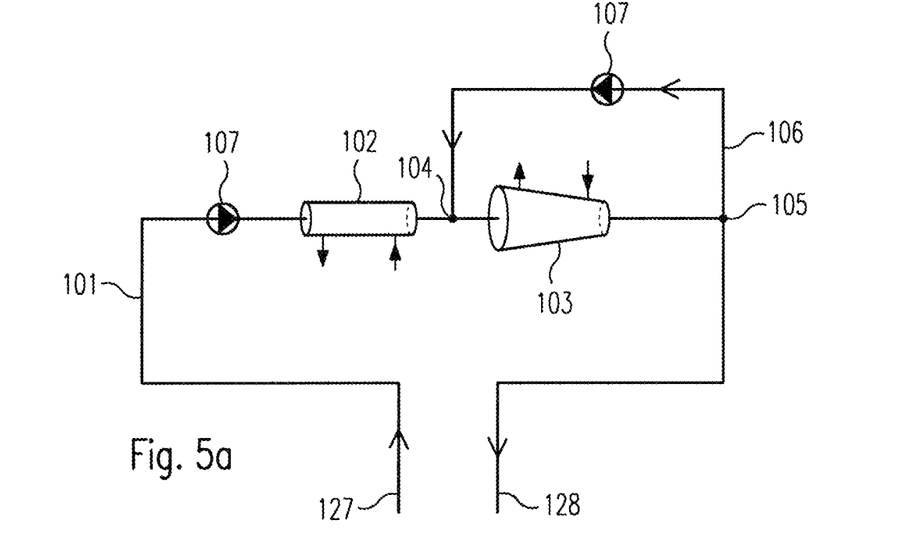
FIG. 5a: shows in a schematic diagram the flow plan a blood guidance device according to the invention in an alternative embodiment.

As shown schematically in FIG. 5*a* on the basis of the flow plan, the blood guidance device 100 may also have an alternative flow guidance. In this example, the first branch 104, at which the secondary line 106 branches off from the main blood line 101, is disposed downstream from the blood treatment element 103. Furthermore, in this example, the second branch 105, at which the secondary line 106 combines with the main blood line 101 again, is disposed upstream from the blood treatment element 103 and downstream from the dialyzer 102.

Figure 5B:
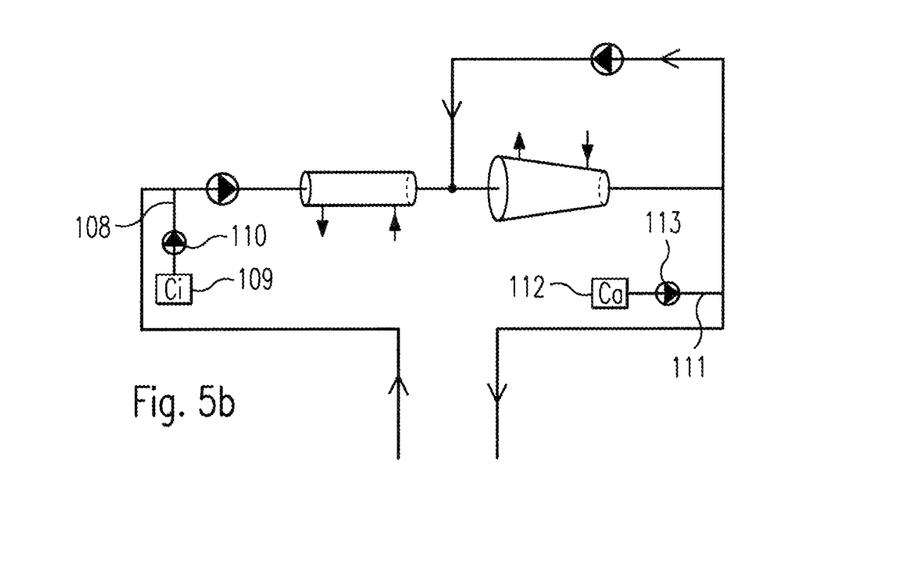
FIG. 5b: shows in a schematic diagram the flow plan of the blood guidance device shown in FIG. 5a with additional optional components.

As shown schematically in FIG. 5*b*, the blood guidance device may optionally have injection ports for medical fluid for anticoagulation. Thus, an injection port 108 for a citrate solution may be disposed upstream from the dialyzer 102. This injection port may also be embodied as a citrate line 108, which is connected to a citrate reservoir 109. Furthermore, the blood treatment device 10 may also have an infusion pump 110, designed to deliver citrate from the reservoir 112 into the main blood line 101 through the injection port 108. An injection port 111 for calcium solution may be disposed downstream from the blood treatment element 103. It may also be designed as a calcium line 111 connected to a calcium reservoir 112. Furthermore, the blood treatment device 10 may have an additional infusion pump 113, designed to deliver calcium out of the reservoir 112 into the main blood line 101 through the injection port 111.

Figure 6A:
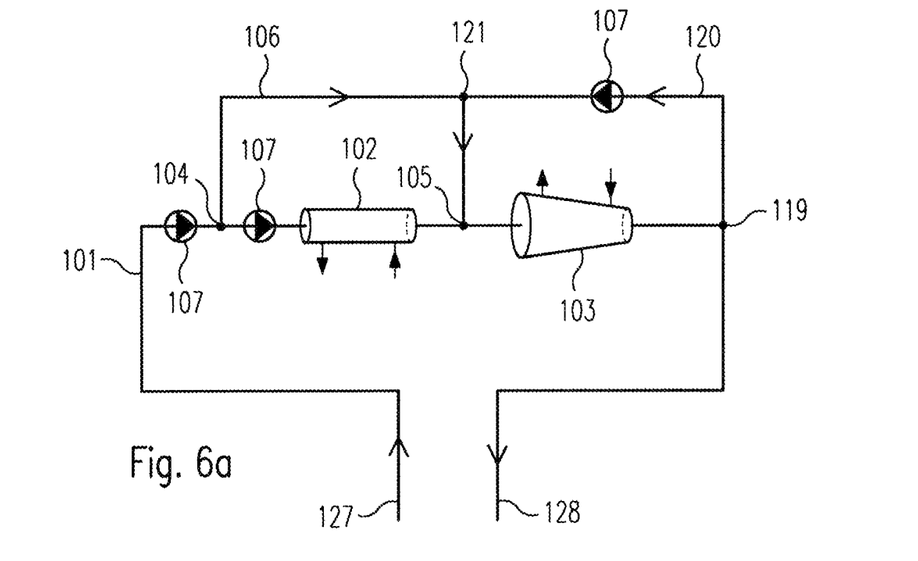
FIG. 6a: shows in a schematic diagram the flow plan of an additional alternative embodiment of a blood guidance device according to the invention.
Figure 6B:
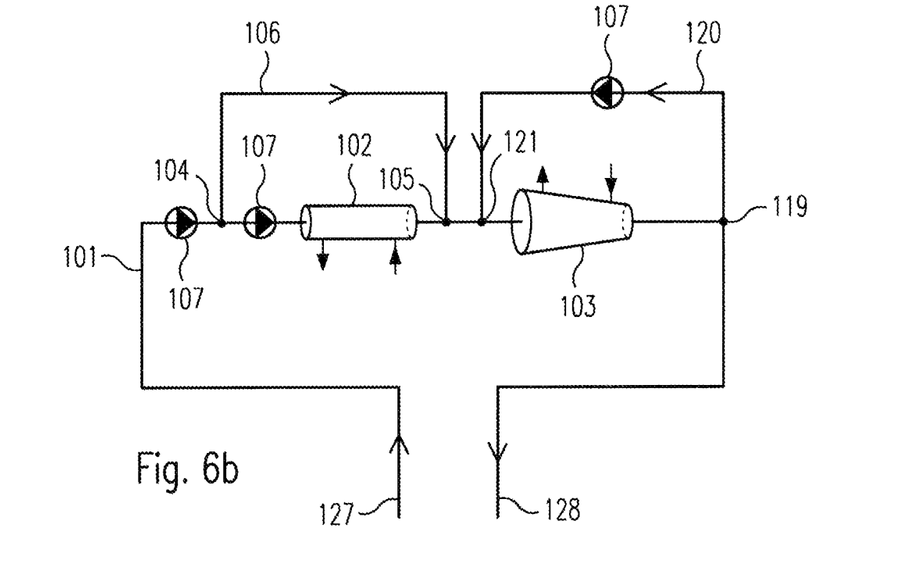
FIG. 6b: shows in a schematic diagram the flow plan of the blood guidance device shown in FIG. 6a with an alternative arrangement of the recirculation return port there.

FIG. 6*a* shows schematically on the basis of the flow plan another alternative embodiment of a blood guidance device according to the invention, wherein a second secondary line 120 for repeated recirculation of the blood through the blood treatment element 103 designed as a gas exchanger here is also present in addition to the features of FIG. 3*a*. The second secondary line 120 leads from a recirculation branch 119 from the main blood line 101 and opens into a recirculation return port 121. In the example of FIG. 6*a*, the recirculation return port 121 is disposed in the first secondary line 106 upstream from the second branch 105. The example in FIG. 6*b* shows an alternative line guidance in this regard and differs from the embodiment illustrated in FIG. 6a in that the recirculation return port 121 is disposed directly in the main blood line 101 downstream from the dialyzer 102 and upstream from the blood treatment element 103. In the embodiments in FIGS. 6a and 6b, the pump configuration 7 of the blood treatment device 10 may also be equipped for generating a blood flow in the second secondary line 120. To do so, the pump configuration 7 of the blood treatment device 10 in FIGS. 6a and 6b—represented here by the pump configuration sections 107—comprises an additional occlusive pump in the second secondary line 120. In addition, the control device 30 of the blood treatment device 10 may be designed to operate the pump configuration 7 in such a way that the blood flow rate in at least one section of the main blood line 101 is independent of at least one of the blood flow rates in the secondary lines 106, 120.

Figure 7:
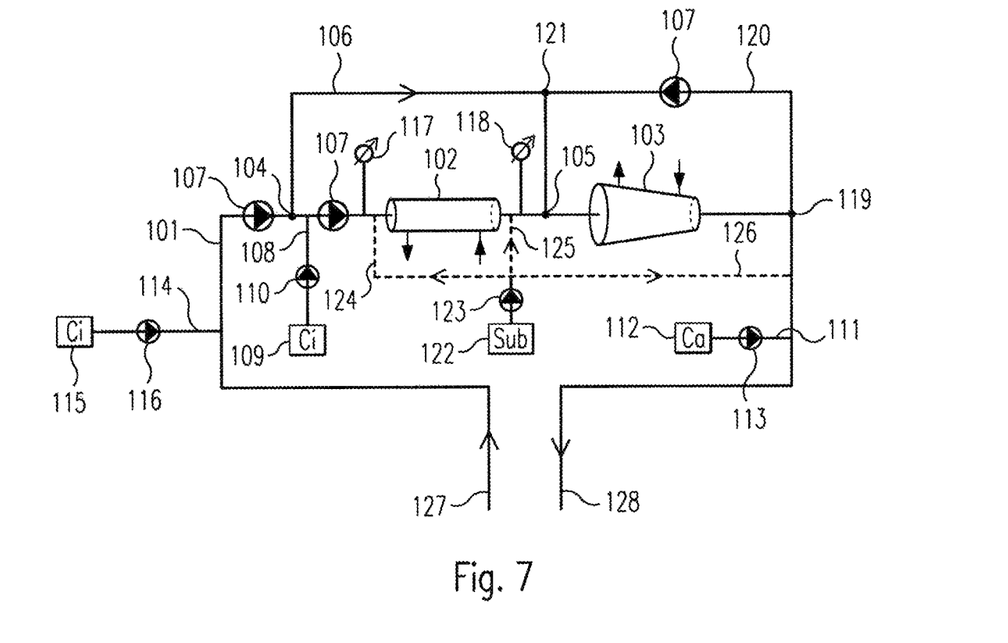
FIG. 7: shows in a schematic diagram the flow plan of the blood guidance device shown in FIG. 6a with additional optional components.

FIG. 7 shows schematically an embodiment of the blood guidance device from FIG. 6a with additional optional components. The injection ports 108, 111, 114 already described for the exemplary embodiment in FIG. 3b as well as the corresponding infusion pumps 110, 113, 116 and reservoirs 109, 112, 115 may also be provided in the embodiment with two secondary lines 106, 120.

FIG. 7 also shows two optional pressure measurements 117, 118 in the main blood line 101 downstream and upstream from the dialyzer 102. First, the pressure downstream from the dialyzer and optionally also upstream from the dialyzer is helpful in determining the transmembrane pressure. This is an important variable which provides information about an imminent filter blockage in the course of dialysis therapy, for example. The transmembrane pressure can also be taken into account in determining the calcium delivery rate via the second injection port 111. Secondly, the pressures in the respective flow sections are also helpful for monitoring the treatment by means of pressure limit value windows.

Furthermore, FIG. 7 shows optional components which allow hemofiltration and/or hemodiafiltration to also take place on the side of renal substitute therapy. To do so the extracorporeal blood circulation may have one or more injection ports 124, 125, 126 for dilution fluid, optionally also designed as a substitute line through which substitution fluid from a reservoir 122 can be fed into the main blood line 101 by means of another infusion pump 123. The substitute line may also be connected in predilution 124, then open upstream from the dialyzer 102 into the main blood line 101. The substitute line may also be connected during post-dilution. In post-dilution, the blood circulation device according to the invention offers two possible connection positions. In a first option, the post-dilution line 125 between the dialyzer 102 and the blood treatment element 103 may open into the main blood line 101. In a second option, the post-dilution line 126 may also open into the main blood line 101 downstream from the gas exchanger. The last variant 126 offers the advantage that the substitution solution which usually contains calcium reduces the anticoagulant effect of the citrate only in the rear portion of the extracorporeal blood circulation.

Alternatively the substitute line may also be intentionally connected by the user to one or more of the aforementioned positions. In a combination of pre- and post-dilution, two infusion pumps that pump the fluid independently of one another are optionally also possible for the dilution fluid (not shown).

The blood treatment device 10 comprises a control device 30. The control device 30 may be configured for controlling and regulating a treatment process. According to one method covered by the invention, in all the embodiments, a blood flow rate between 0 and 300 mL/min can be created in the main blood line 101 in the area of the dialyzer 102 by means of the pump configuration 7. In addition, a blood flow rate of more than 500 mL/min can be created in the area of the blood treatment element 103. In the example in FIGS. 3a and 3b, the flow rate in the main blood line 101 upstream from the first branch 104 corresponds to the flow rate in the blood treatment element 103. The desired dialysate flow rate can be adjusted by means of the pump configuration 7. This yields the flow rate in the secondary line 106 as the difference between the flow rate in the blood treatment element 103 and in the dialysate flow rate.

The flow rate in the blood treatment element 103 may also be great than 800 mL/min, greater than 1 mL/min or greater than 2 L/min in all embodiments of the invention. ECMO methods are generally used with blood rates of up to 8 L/min. All these flow rates and even higher flow rates are possible according to the invention in the area of a blood treatment element 103 which is designed as a gas exchanger, for example.

The dialyzer flow rate may also be in the range between 100 and 250 mL/min in all embodiments. It may also be in the range of 175 to 225 mL/min or may be exactly 200 mL/min.

The flow rate of the first medical fluid for anticoagulation, for example, citrate, which is pumped by means of the first infusion pump 110 into the main blood line 101, may be regulated by the control device 30 as a function of the dialyzer flow rate.

The flow rate of the second medical fluid for anticoagulation, for example, calcium, which is pumped by means of the second infusion pump 113 into the main blood line 101, can be regulated by the control device 30 as a function of the dialyzer flow rate. The regulation may additionally take into account other dependencies such as, for example, the flow rate of the first medical fluid for anticoagulation, the flow rate of the third medical fluid for anticoagulation, the transmembrane pressure (TMP), the type of dialyzer and/or other parameters, optionally also those to be selected or entered by the user.

The flow rate of the third medical fluid for anticoagulation, for example, citrate, can be controlled by means of direct selection by the user. It may also be regulated as a function of the flow rate in the blood treatment element 103 or it may be regulated as a function of the difference between the flow rate in the blood treatment element 103 and the dialyzer flow rate.

The invention claimed is:

1. A system for treatment of blood, comprising a blood treatment device and a blood guidance device for cooperating with the blood treatment device, wherein
the blood treatment device comprises:
a control device; and
a pump configuration, and
the blood guidance device comprises:
a dialyzer;
a main blood line connected, for fluid communication, to the dialyzer at a dialyzer connection point, and connected, for fluid communication, to a blood treatment element at a blood treatment element connection point downstream from the dialyzer, wherein the main blood line has, at a first end, a blood withdrawal port for connection to a blood withdrawal access of a patient, and, at a second end, has a blood return port for connection to a blood return access of the patient;

a first secondary line that branches off from the main blood line at a first branch, and recombines with the main blood line at a second branch; and one or more pump configuration sections on which act the pump configuration of the blood treatment device, wherein the first branch is disposed upstream from the dialyzer connection point, and the second branch is disposed downstream from the dialyzer connection point and upstream from the blood treatment element connection point.

2. The system for treatment of blood according to claim 1, further comprising a second secondary line that branches off from the main blood line at a recirculation branch and opens into a recirculation return port, wherein the first branch is disposed upstream from the dialyzer connection point, and the second branch is disposed downstream from the dialyzer connection point and upstream from the blood treatment element connection point, and the recirculation branch is disposed downstream from the blood treatment element connection point, and either (1) the recirculation return port is disposed in the main blood line upstream from the blood treatment element connection point and downstream from the dialyzer connection point, or (2) the recirculation return port is disposed in the first secondary line upstream from the second branch.

3. The system for treatment of blood according to claim 1, wherein the main blood line comprises:

an injection port for a first medical fluid for anticoagulation, upstream from the dialyzer connection point; and/or an injection port for a second medical fluid for anticoagulation, downstream from the blood treatment element connection point.

4. The system for treatment of blood according to claim 1, wherein the main blood line comprises:

an injection port for a first medical fluid for anticoagulation downstream from the first branch and upstream from the dialyzer connection point; and/or an injection port for a second medical fluid for anticoagulation downstream from the blood treatment element connection point; and/or an injection port for a third medical fluid for anticoagulation upstream from the first branch.

5. The system for treatment of blood according to claim 1, wherein the main blood line has a pressure measurement section for determining the pressure in the main blood line downstream from the dialyzer connection point and upstream from the blood treatment element connection point.

6. The system for treatment of blood according to claim 1, wherein the main blood line comprises:

an injection port for a dilution fluid, upstream from the dialyzer connection point; and/or an injection port for a dilution fluid, downstream from the dialyzer connection point and upstream from the blood treatment element connection point; and/or an injection port for a dilution fluid, downstream from the blood treatment element connection point.

7. The system for treatment of blood according to claim 1, wherein the blood comprises the dialyzer and the blood treatment element.

8. The system for treatment of blood according to claim 7, wherein the blood treatment element is a gas exchanger.

* * * * *